United States Patent
Kloster

(10) Patent No.: US 9,693,847 B2
(45) Date of Patent: Jul. 4, 2017

(54) SEAL FOR TEETH WHITENING TRAYS

(71) Applicant: KONINKLIJKE PHILIPS N.V., Eindhoven (NL)

(72) Inventor: Tyler G. Kloster, Snoqualmie, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 7 days.

(21) Appl. No.: 14/442,110

(22) PCT Filed: Dec. 9, 2013

(86) PCT No.: PCT/IB2013/060742
§ 371 (c)(1),
(2) Date: May 12, 2015

(87) PCT Pub. No.: WO2014/097046
PCT Pub. Date: Jun. 26, 2014

(65) Prior Publication Data
US 2016/0287365 A1  Oct. 6, 2016

Related U.S. Application Data

(60) Provisional application No. 61/738,587, filed on Dec. 18, 2012.

(51) Int. Cl.
*A61C 17/00* (2006.01)
*A61C 19/06* (2006.01)
*A61F 13/02* (2006.01)
*A61C 5/90* (2017.01)

(52) U.S. Cl.
CPC ............. *A61C 19/066* (2013.01); *A61C 5/90* (2017.02); *A61F 13/02* (2013.01)

(58) Field of Classification Search
CPC .......... A61C 19/066; A61C 5/14; A61F 13/02
USPC ....................................... 433/37, 216, 217.1
See application file for complete search history.

(56) References Cited

U.S. PATENT DOCUMENTS

| | | | | |
|---|---|---|---|---|
| 5,323,787 | A | * 6/1994 | Pratt | A61C 19/063 128/859 |
| 5,575,654 | A | 11/1996 | Fontenot | |
| 5,980,249 | A | * 11/1999 | Fontenot | A61C 19/02 433/215 |
| 6,274,122 | B1 | * 8/2001 | McLaughlin | A61C 19/063 128/860 |
| 6,343,932 | B1 | * 2/2002 | Wiesel | A61O 5/00 424/435 |

(Continued)

FOREIGN PATENT DOCUMENTS

| | | |
|---|---|---|
| CN | 1571654 A | 1/2005 |
| CN | 1913867 A | 2/2007 |
| WO | 03015656 A2 | 2/2003 |

*Primary Examiner* — Pedro Philogene
*Assistant Examiner* — David C Comstock

(57) ABSTRACT

A teeth whitening appliance (10) such as a tray includes a seal member (18) which is attached to an interior surface (19) of the tray. The seal member comprises a fabric strip or a gecko adhesive strip which extends around the periphery of the interior surface of the tray adjacent the peripheral or boundary edge thereof. The seal member adheres to the teeth, so as to prevent gel from escaping from the tray when the tray is in place, as well as preventing water/saliva in the mouth from entering the tray, while also being convenient to remove.

15 Claims, 2 Drawing Sheets

(56) References Cited

U.S. PATENT DOCUMENTS

| | | | |
|---|---|---|---|
| 6,689,344 B2* | 2/2004 | Chang | A61K 8/0208 |
| | | | 424/53 |
| 6,997,708 B2* | 2/2006 | Allred | A61O 5/00 |
| | | | 433/215 |
| 2005/0186150 A1 | 8/2005 | Allred et al. | |
| 2007/0282247 A1* | 12/2007 | Desai | A61L 27/54 |
| | | | 604/19 |
| 2007/0298380 A1 | 12/2007 | Allred | |
| 2009/0136893 A1 | 5/2009 | Zegarelli | |

* cited by examiner

SEAL FOR TEETH WHITENING TRAYS

CROSS-REFERENCE TO PRIOR APPLICATIONS

This application is the U.S. National Phase application under 35 U.S.C. §371 of International Application No. PCT/IB32013/060742, filed on Dec. 9, 2013, which claims the benefit of U.S. Provisional Patent Application No. 61/738,587, filed on Dec. 18, 2012. These applications are hereby incorporated by reference herein.

TECHNICAL FIELD

This invention relates generally to teeth whitening appliances, and more specifically concerns an accessory for teeth whitening trays, mouthpieces and strips.

BACKGROUND OF THE INVENTION

In general, appliances for use in teeth whitening are well known. These include mouthpieces, strips and in particular teeth whitening trays, all of which are adapted to receive teeth whitening gel. The appliance is then applied to the teeth for a selected period of time in order to accomplish teeth whitening. The teeth whitening gel itself can be any one of various known compositions, and does not form a part of the present invention.

None of the known teeth whitening appliances have a structure to seal the perimeter of the appliance. Hence, present teeth whitening appliances, for instance a tray, allow saliva to intrude into the tray and thus dilute or wash the gel from the tray, reducing the whitening effect of the gel in the tray. Further, the lack of a seal on such appliances also allows the gel to seep out from the appliance. Since the teeth whitening gel used typically contains peroxide, this can result in irritation of the gums, as well as an undesirable taste.

SUMMARY OF THE INVENTION

Accordingly, a whitening appliance, comprises: a teeth whitening appliance for holding teeth whitening gel, wherein the appliance has an interior surface which comes adjacent the front portion of selected teeth of a user; and a seal member attached to the interior surface of the appliance, the seal member comprising a fabric strip member which extends around the periphery of the interior surface of the appliance and adheres to the teeth by absorbing water or saliva present in the mouth sufficient to create a surface tension which adheres and seals the appliance to the teeth, but which permits convenient removal from the teeth.

Also, a teeth whitening appliance, comprises: a teeth whitening appliance for holding teeth whitening gel, wherein the appliance has an interior surface which comes adjacent the front portion of selected teeth of a user; and a seal member attached to the interior surface of the appliance, the seal member comprising a gecko adhesive strip for removably adhering the appliance to the teeth.

BEST MODE FOR CARRYING OUT THE INVENTION

Figure 1:
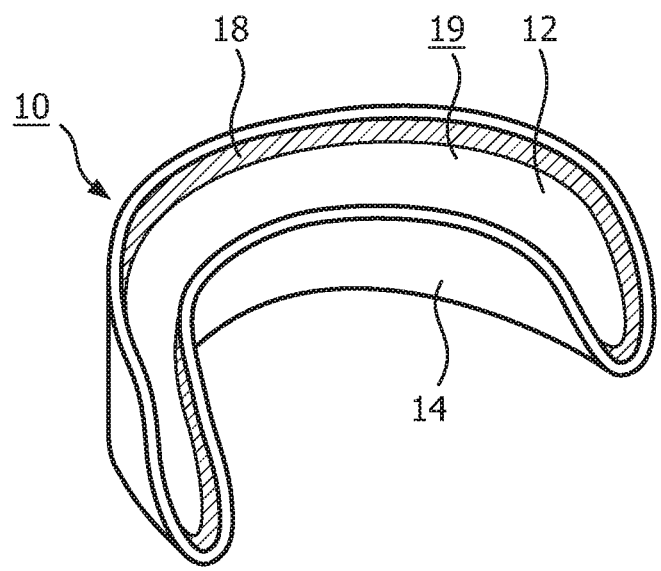
FIG. 1 is an isometric view of a teeth whitening tray with one embodiment of a seal member in place.
Figure 2:
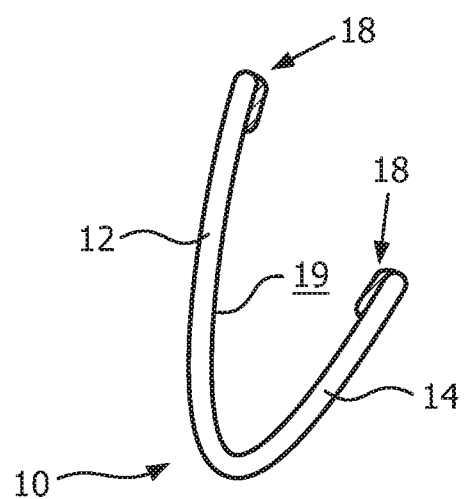
FIG. 2 is a cross sectional diagram of the teeth whitening tray with seal member of FIG. 1.

FIGS. 1 and 2 show an isometric view and a cross sectional view of a teeth whitening tray with a seal member in place. The teeth whitening tray is shown generally at 10 and is shown in a formed configuration adapted to receive the teeth of a user. The teeth whitening tray 10 generally comprises a soft plastic material for comfort and includes a forward portion 12 covering the front surface of the teeth to be whitened, and a rear portion 14 covering at least a part of the rear surface of the same teeth, with the forward and rear portions being joined together to form a unitary tray with an interior surface 19. The details of the tray structure are disclosed in more detail in a co-pending application owned by the assignee of the present invention. The tray could, although not necessarily, include an embedded metal strip or mesh which allows the tray to be formed to the dentition configuration of an individual user. White a tray is shown for illustration, the whitening appliance could be a mouthpiece or a strip member A seal member 18 extends continuously around the periphery of the interior surface of the tray. The seal member thus borders the peripheral edge of the interior surface of the tray. In one embodiment, the seal member 18 is a thin fabric strip which is attached to or a part of the interior surface of the tray. It could be integral with the tray. The cloth can be any of various fabrics which are capable of absorbing water/saliva, including cotton and other fabrics. The result is shown in FIGS. 1 and 2.

The seal member 18 is typically strongly attached to the tray or embedded therein. In use, the water/saliva in the mouth is absorbed into the cloth, sufficient to produce a surface tension between the cloth and the tray which efficiently and reliably adheres the tray to the teeth, maintaining the tray with the gel therein on the teeth to accomplish the desired whitening. The fabric strip comprising the seal member acts as a semi-permeable membrane with the absorbed water/saliva to produce the necessary surface tension.

Figure 3:
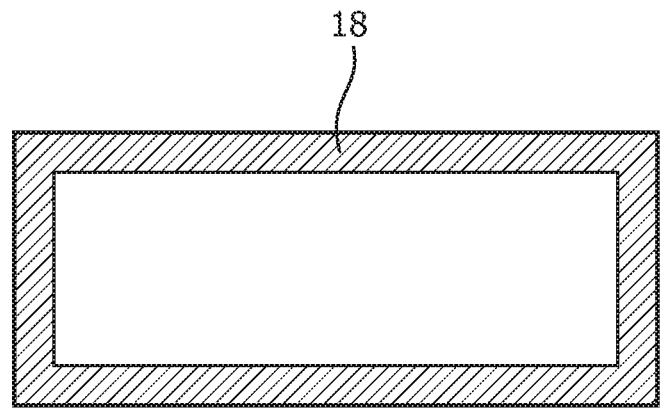
FIG. 3 is an elevational view of the seal member by itself.

While such a structure will not prevent all saliva from outside the seal member entering into the tray, it will substantially prevent entry of such saliva, due to the aspect ratio of the member, being wider than thick, in this case 2-4 mm wide and 0.2 mm thick, as shown for example in FIG. 3.

This arrangement will prevent most of the saliva in the mouth outside the seal from reaching the peroxide gel in the tray, as well as prevent the peroxide gel boundaried by the seal from migrating out of the tray. The tray, mouthpiece or strip with the seal member is thus convenient to apply to and remove from the teeth by a user.

Figure 4:
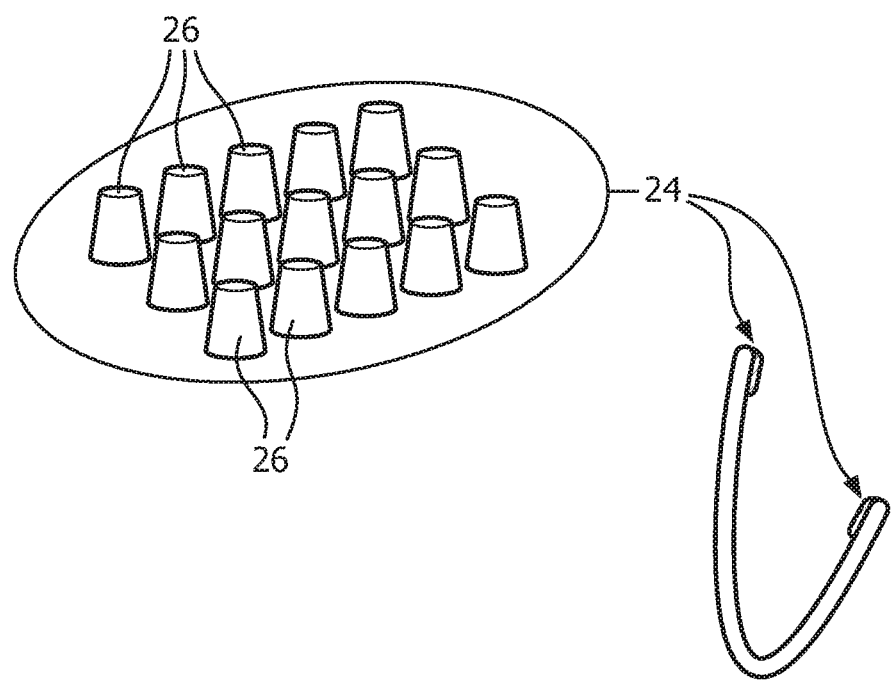
FIG. 4 is an isometric view of another embodiment of a seal member using gecko adhesive elements.

Another embodiment, shown in FIG. 4, includes a synthetic gecko adhesive strip or member 24 positioned around the perimeter of the tray or strip. Gecko adhesives use thousands of tiny hair-like spatulas 26-26, 1-5 microns, on their feet and surface molecules to stick to a surface through van der Waals forces. The gecko adhesive removably attaches the tray to the teeth.

With the seal member in place as part of the tray, mouthpiece or strip, the user places the appliance in their mouth and with fingers presses the tray or other appliance onto the teeth/gums. The tray is thus effectively sealed to the teeth. When the treatment is completed, the tray or other appliance is removed from the mouth and rinsed with water so that it is ready to use again. The appliance could also be single use and disposable. While the appliance has been generally described as a tray, it could be a mouthpiece, strip or other appliance.

Although a preferred embodiment has been disclosed for purposes of illustration, it should be understood that various changes, modifications and substitutions may be incorporated in the preferred embodiment without departing from the spirit of the invention as defined by the claims which follow:

The invention claimed is:

1. A teeth whitening appliance, comprising:
   a teeth whitening appliance for holding teeth whitening gel, wherein the appliance has an interior surface which comes adjacent the front portion of selected teeth of a user; and
   a seal member attached to the interior surface of the appliance, the seal member comprising a fabric strip member which extends around the entire periphery of the interior surface of the appliance and adheres to the teeth by absorbing water or saliva present in the mouth to create a surface tension which adheres and seals the appliance to the teeth, but which permits removal when the appliance is pulled away from the teeth.

2. The appliance of claim 1, wherein the selected teeth are the front teeth.

3. The appliance of claim 1, wherein the appliance is a tray, arranged and configured so that the interior surface thereof comes adjacent the front portion of the selected teeth and a portion of the rear surface of the teeth.

4. The appliance of claim 3, wherein the tray is formable to the teeth configuration of the user.

5. The appliance of claim 1, wherein the fabric strip has an aspect ratio of 2-4 mm wide by approximately 0.2 mm thick.

6. The appliance of claim 1, wherein the surface tension adhesion force produces a strong enough seal to prevent migration of water/saliva into the tray and to prevent peroxide gel from migrating out of the tray, while permitting removal of the appliance from the teeth when the appliance is pulled away from the teeth.

7. The appliance of claim 1, wherein the appliance is a whitening strip.

8. The appliance of claim 1, wherein the appliance is a mouthpiece.

9. The appliance of claim 1, wherein the fabric strip is cotton.

10. A teeth whitening appliance, comprising:
    a teeth whitening appliance for holding teeth whitening gel, wherein the appliance has an interior surface which comes adjacent the front portion of selected teeth of a user; and
    a seal member attached to the interior surface of the appliance, the seal member comprising a gecko adhesive strip for removably adhering the appliance to the teeth, the seal member extending around the entire periphery of the interior surface of the appliance.

11. The appliance of claim 10, wherein the selected teeth are the front teeth.

12. The appliance of claim 10, wherein the appliance is a tray, arranged and configured so that the interior surface thereof comes adjacent the front portion of the selected teeth and a portion of the rear surface of the teeth.

13. The appliance of claim 12, wherein the tray is formable to the teeth configuration of the user.

14. The appliance of claim 10, wherein the surface tension adhesion force produces a strong enough seal to prevent migration of water/saliva into the tray and to prevent peroxide gel from migrating out of the tray, while permitting removal of the appliance from the teeth when the appliance is pulled away from the teeth.

15. The appliance of claim 10, wherein the appliance is a mouthpiece.

* * * * *